(12) United States Patent
Peterfeso et al.

(10) Patent No.: US 6,240,322 B1
(45) Date of Patent: May 29, 2001

(54) SYSTEM AND APPARATUS HAVING LOW PROFILE COLLAPSIBLE TINES

(75) Inventors: Randall M. Peterfeso; Mary Lee Cole, both of St. Paul; Larry L. Hum, Cottage Grove; Michael P. Campbell, New Brighton, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/186,326

(22) Filed: Nov. 4, 1998

(51) Int. Cl.⁷ .................................................. A61N 1/05
(52) U.S. Cl. ............................................ 607/126; 607/128
(58) Field of Search ..................................... 607/126, 128

(56) References Cited

U.S. PATENT DOCUMENTS

| | | | |
|---|---|---|---|
| 4,564,023 | * 1/1986 | Hess | 607/126 |
| 4,945,922 | 8/1990 | van Krieken . | |
| 4,957,118 | 9/1990 | Erlebacher . | |
| 5,282,838 | * 2/1994 | Hauser et al. | 607/9 |
| 5,545,206 | 8/1996 | Carson . | |
| 5,554,178 | 9/1996 | Dahl et al. . | |
| 5,578,068 | 11/1996 | Lasko et al. . | |
| 5,868,741 | * 2/1999 | Chia et al. . | |
| 5,931,864 | * 8/1999 | Chastain et al. | 607/128 |
| 5,957,966 | * 9/1999 | Schroeppel et al. | 607/122 |
| 6,006,139 | * 12/1999 | Kruse et al. . | |

FOREIGN PATENT DOCUMENTS

| | | | |
|---|---|---|---|
| 0057877 | 8/1982 | (EP) | 607/121 |
| 0546414 | 12/1991 | (EP) . | |
| 0779080 | 12/1995 | (EP) . | |
| 2067411 | 1/1980 | (GB) . | |
| 2099307 | 12/1982 | (GB) . | |

* cited by examiner

*Primary Examiner*—Carl H. Layno
(74) *Attorney, Agent, or Firm*—Schwegman, Lundberg, Woessner & Kluth, P.A.

(57) ABSTRACT

A medical device is insertable and/or implantable into a body of a patient. The medical device includes a plurality of hollow and/or collapsible tines which are adapted to assist in deployment of the medical device into the body and in preventing inadvertent removal or dislodging of the medical device from the body. The tines are coupled to the medical device body at a coupling end and extend away from the device to a free end. The tines can have a number of configurations such as cylindrical or cone shaped. In addition, the cross section of the free end of the tines can be elliptical, where the free end extends to a tip. Another cross section includes a semi-circle including an open portion which can face towards or away from the medical device body. The tines also include coiled structures which can have a radial axis perpendicular to the radial axis of the medical device.

32 Claims, 7 Drawing Sheets

SYSTEM AND APPARATUS HAVING LOW PROFILE COLLAPSIBLE TINES

FIELD OF THE INVENTION

The present invention relates generally to medical devices. More particularly, it pertains to insertable medical instruments having low profile, collapsible tines.

BACKGROUND OF THE INVENTION

Electrodes have been implanted in the body for electrical cardioversion or pacing of the heart. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm.

Cardiac pacing may be performed by the transvenous method or by electrodes implanted directly onto the epicardium. Transvenous pacing may be temporary or permanent. In temporary transvenous pacing an electrode catheter is introduced into a peripheral vein and fluoroscopically positioned against the endocardium. Traditional permanent transvenous pacing is performed under sterile surgical conditions where an electrode is positioned in the right ventricle or atrium through a subclavian vein, and the proximal terminals are attached to a pulse generator which is implanted subcutaneously. However, for certain conditions, for example, congestive heart failure or to improve hemodynamics, it can be more beneficial to couple the electrode with the left ventricle or the left atrium. This placement can provide stimulation of the left side only, or when used with a right sided lead can be used for biventricular pacing.

Lead placement within the left ventricle or left atrium, however, has been considered as involving more risk than lead placement within the right ventricle or right atrium since the left chambers involve pumping at higher pressures. In addition, the course of blood from the left ventricle to the body involves systemic circulation, where blood flows to several organs other than the lungs, such as the brain. Potential complications with blood clots which can be induced by the presence of the lead preclude lead implantation within left chambers of the heart. One approach to resolve this issue is to place the lead outside of the heart proximate the left ventricle or the left atrium. Traditionally, To attach a lead epicardially, a thoracotomy is performed where the thorax is opened to obtain access to the heart. This procedure involves painfuil and expensive surgery for the patient.

Accordingly, what is needed is a medical device for coupling with a portion of the heart. What is further needed is a lead which can be implanted within veins adjacent to the heart. What is also needed is a lead which minimizes drag during lead placement.

SUMMARY OF THE INVENTION

A medical device is provided which is adapted to be placed intravenously with minimal drag during placement of the medical device. The medical device includes retaining features which collapse during insertion of the medical device, and prevent inadvertent removal of the medical device from the body. In one embodiment, the medical device includes a lead having a distal tip electrode which is adapted for implantation about the heart. The electrode includes at least one tine, which, in one embodiment, is at least partially hollow. In another embodiment, the at least one tine is formed of a foam material. In one embodiment, the tine is tapered from a free end to a coupling end. Alternatively, the tine has a cylindrical structure. The tine has a thin-walled structure, which in one configuration comprises a semi-circular cross-section. The semi-circular cross-section can be disposed with the open section faces towards or away from the body of the electrode, depending on the embodiment.

Each tine is coupled with the medical device at a coupling end, where a free end is adapted to engage with structure encompassing the medical device after implantation, should a removing force be inadvertently applied to the device. The tine is coupled to the device in a number of manners, such as molding the tine to the device, bonding the tine to the device, or a mechanical attachment such as a compression fit or a snap fit. The tine can also be coupled with the lead within a recess to allow for further collapsibility. The tine is, in one embodiment, formed from pliable material such as silicone. Alternatively, a bioresorbable material, a foam, or other pliable polymer can be used to form the tine. In another embodiment, other materials or shapes which allow for collapsibility could also be used.

In another configuration, a distal tip electrode is provided which is adapted for implantation about the heart. The electrode includes an electrode assembly which has one or more tines. The tine radially extends from a coupling end which is coupled with a lead body of the electrode assembly. The tine radially extends from the coupling end to a free end.

In yet another embodiment, a system is provided for monitoring or stimulating cardiac activity. The system includes a pulse sensor and signal generator coupled with a lead. The lead extends from a proximal end to a distal end, where the proximal end is operatively coupled with the pulse sensor and signal generator. An electrode assembly is coupled with the lead, which includes an electrode and at least one hollow tine. The tine is adapted to collapse upon insertion into an encompassing structure, such as a vein or introducer.

Collapsible tines aid in providing an implantable medical device which is atraumatic to the vessel walls, and also provides resistance to inadvertent dislodgement of the medical device from the patient. The collapsible feature of the medical device also allows for a smaller introducer to be used for a patient which provides for a less traumatic implant for the patient. In addition, deployment of the medical device is improved since the amount of drag is reduced as the lead is passed through a vein. This allows for flexibility in insertion of a medical device, such as a lead through restricting structures.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1A:
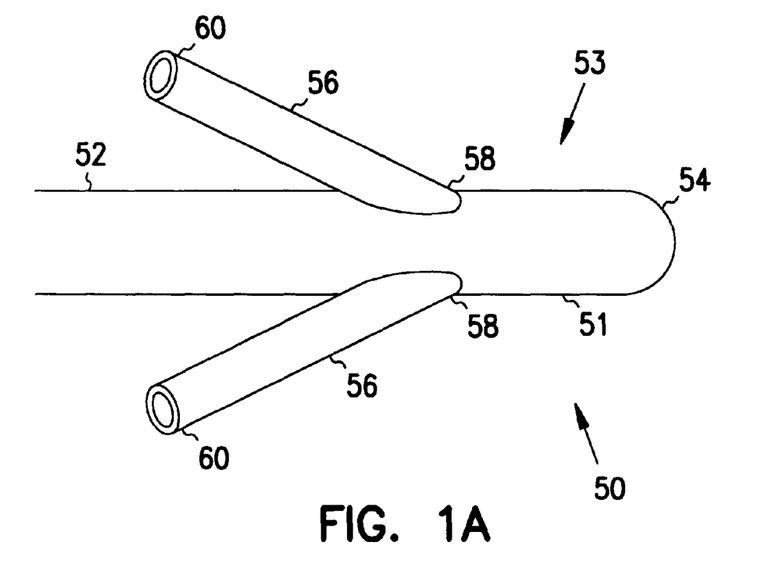
FIG. 1A is an elevational view illustrating a distal tip electrode constructed in accordance with one embodiment of the present invention.

A medical device is provided which has at least one low profile, collapsible tine. The collapsible tines collapse to a low profile when the medical device is passed through restricting diameters, for example, through an introducer or vasculature. The tines also provide for a mechanism which anchors the medical device and prevents the medical device from becoming inadvertently dislodged from the patient. A first embodiment is illustrated in FIG. 1A, and a second embodiment in FIG. 1B. A medical device 50, such as a lead, has a body 52 which extends, in one embodiment, to a tapered portion 54. In another configuration, the medical device 50 comprises a lead which includes an electrode assembly 51. The tines 56 are coupled with a portion of the body 52, as will be further described below.

Figure 1B:
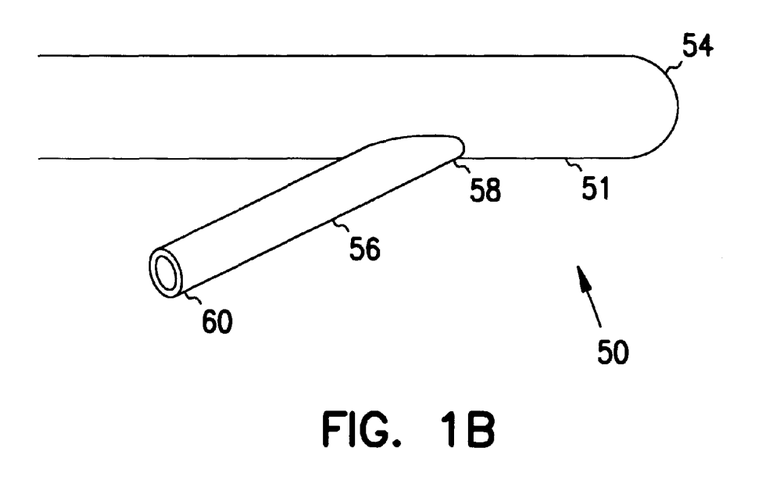
FIG. 1B is an elevational view illustrating a distal tip electrode constructed in accordance with another embodiment of the present invention.

The plurality of tines 56, in one configuration, comprise hollow cylinders as shown in the drawing, where the plurality of tines 56 are at least partially hollow. The inner features of the plurality of tines 56 are not limited to that shown, and can comprise other configurations as well. The hollow tines 56 comprise a thin wall structure which, in one configuration, has a circular cross section. The first end 58 of each of the tines 56 is coupled with the body 52 of the medical device 50. Each of the plurality of tines 56 extends from the first end 58 to the second end 60, which second end 60 is free from the body 52 of the medical device 50. In one embodiment, the tines 56 are tapered from the second end 60 to the first end 58. When unrestricted by, for example, a vasculature, as shown in the drawing, each of the tines 56 are angled away from the body 52 such that each of the tines 56 are adapted for anchoring the medical device 50 within an encompassing structure, such as a vein or ventricular trabecula. In another configuration, each of the tines 56 is only partially hollow. Although a plurality of tines 56 are discussed, the medical device 50 comprises, in one embodiment, at least one tine 56, as shown in FIG. 1B.

Figure 2A:
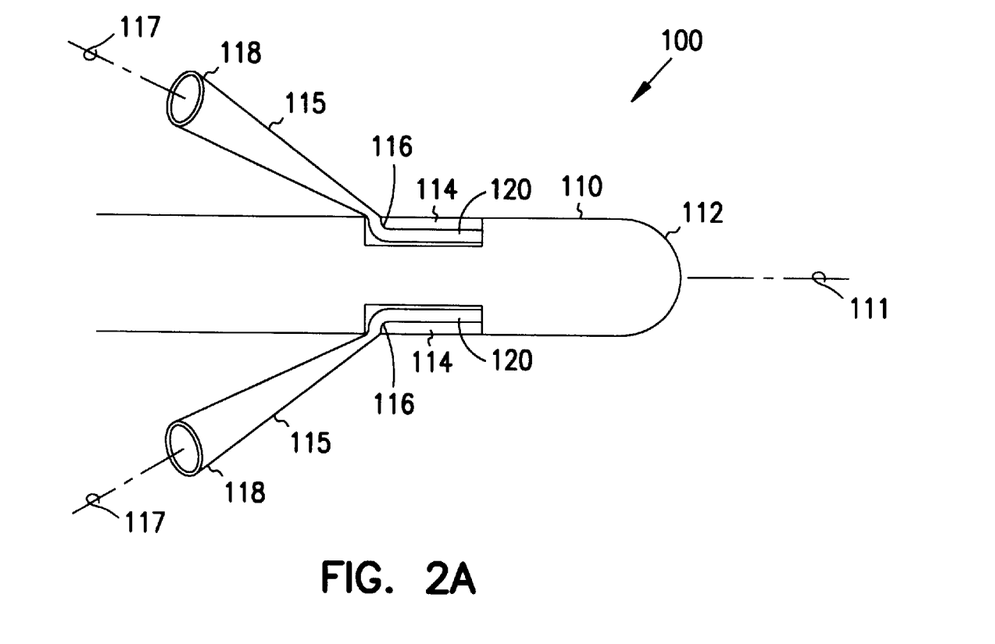
FIG. 2A is an elevational view illustrating a distal tip electrode constructed in accordance with yet another embodiment of the present invention.
Figure 2B:
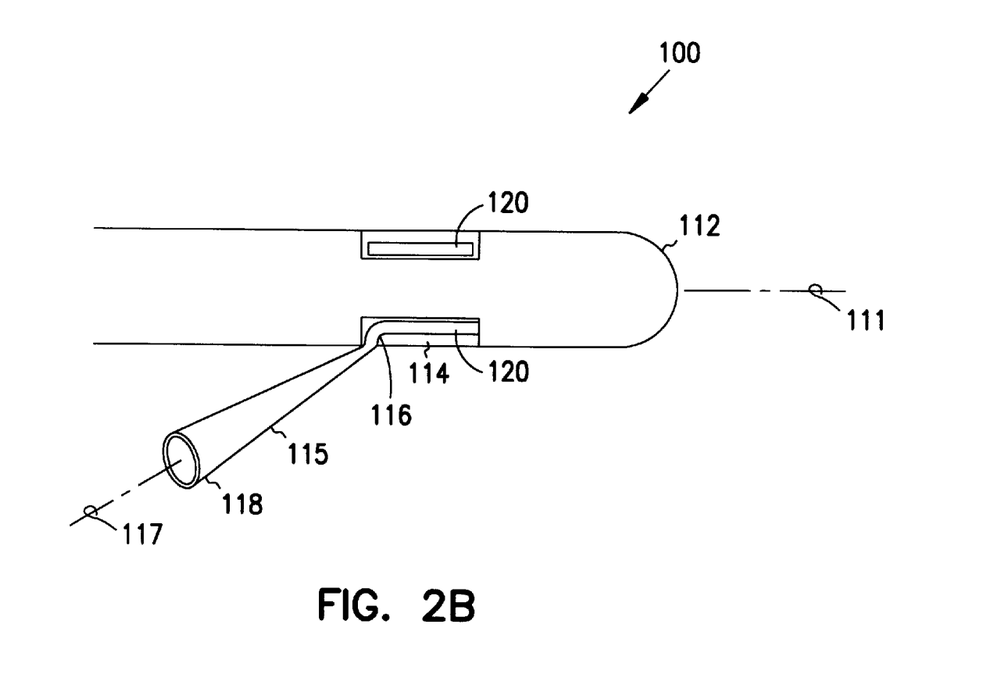
FIG. 2B is an elevational view illustrating a distal tip electrode constructed in accordance with one embodiment of the present invention.

FIGS. 2A and 2B illustrate another embodiment of a medical device 100, which in one embodiment includes a lead. The medical device 100 has a body 110 which is disposed about a radial axis 111. In one configuration, the body 110 includes a tapered portion 112 which facilitates insertion of the medical device 100 into a patient. In one embodiment, the medical device 100 includes at least one tine 115. In another embodiment, the medical device 100 includes a plurality of tines 115 which are coupled with at least a portion of the body 110. The body 110 has, in one embodiment, at least one recess 114 (FIG. 2B). In another embodiment, as shown in FIG. 2A, the body 10 has a recess 114 for each of the plurality of tines 115.

Each of the plurality of tines 115 extends from a coupling end 116 to a free end 118. The coupling end 116 is adapted to be attached to the body 110 of the medical device 100. In one embodiment, the coupling end 116 includes a ring 120, which secures the coupling end 116 and is itself secured to the body 110 of the medical device 100. In yet another configuration, the ring 120 is used to secure multiple tines 115 to the body 110 within the recess 114. Having the coupling end 116 of the tines 115 disposed within the recess 114 assists in a smoother insertion of the medical device 100.

Each of the plurality of tines 115, in one embodiment, is angled away from the body axis 111 of the body 110. The plurality of tines 115 are defined in part by their each radial axis 117. In one configuration, as each of the tines 115 extends from the coupling end 116 to the free end 118, the tines 115 are tapered from the free end 118 to the coupling end 116. In another embodiment, a cross section of a diameter proximate the coupling end 116 is smaller than the cross section of the free end 118. In yet another configuration, each of the tines 115 forms a cone shape as the tines extend from the coupling end 116 to the free end 118. In yet another configuration, each of the tines 115 has a circular cross section proximate the free end 118. The tines 115 are at least partially hollow and in one configuration have a thin-walled structure. The tubular design in combination with the hollow structure, allows for the tines 115 to offer rigidity as well as collapsibility during implantation. Although a plurality of tines 115 are discussed, the medical device 100 comprises, in one embodiment, at least one tine 115, as shown in FIG. 2B.

Figure 3:
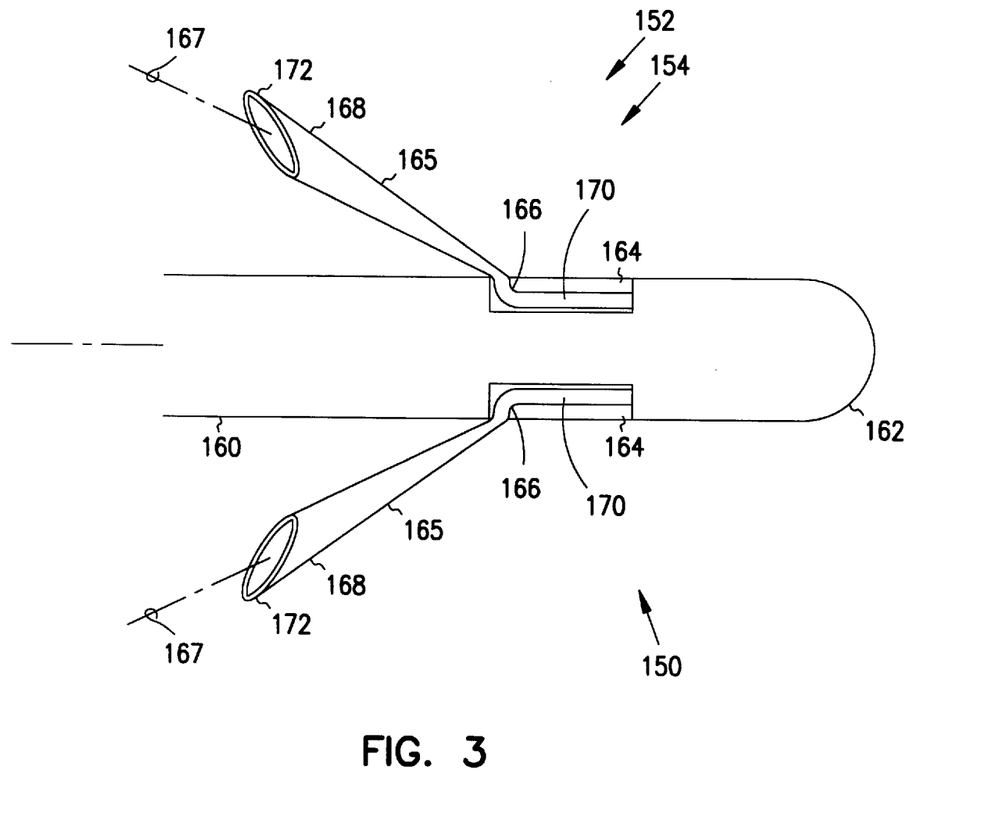
FIG. 3 is an elevational view illustrating a distal tip electrode constructed in accordance with yet another embodiment of the present invention.

FIG. 3 illustrates another embodiment of the present invention, which shows a medical device 150. The medical device 150 in one embodiment comprises a lead 152. In one configuration the lead 152 includes an electrode assembly 154. The medical device 150 is defined in part by a body 160 which extends to a tapered portion 162, in one embodiment. The medical device 150 also includes at least one tine 165.

In another configuration, a plurality of tines 165 are provided with the medical device 150. Each of the tines 165 extends from a coupling end 166 to a free end 168. Each of the tines 165 are coupled with the body 160 of the medical device 150 at the coupling end 166. The tines 165 can be coupled in a number of manners. For example, in one embodiment the tines 165 are molded to the body 160 of the medical device 150. Alternatively, in yet another configuration, the tines 165 are bonded to the medical device. The tines 165 can also be attached to the medical device 150 using a mechanical attachment, such as snap-fit.

Each of the tines 165 are at least partially hollow, in one embodiment, and each is defined in part by a radial axis 167. In another configuration, each of the tines 165 is substantially hollow where the tines 165 have a thin-walled structure. Each of the tines 165 extends away from the body 160 to the free end 168 such that each of the tines 165 is angled away from the body 160 of the medical device 150 before the medical device 150 is implanted into a patient. In another configuration, the body 160 includes at least one recess 164. For this configuration, an individual tine 165 is disposed in an individual recess 164 at the coupling end 166 of each of the tines 165.

Proximate to the coupling end 166 of the tines 165, in one embodiment, the tines 165 have flats 170, which are adapted to be received by each recess 164. Proximate the free end 168, in another embodiment, the tines have an elliptical cross section as shown in FIG. 3, where the free end 168 is cut at an angle relative to the body 160. Having the elliptical cross section provides for a tip 172 at the distal end or the free end 168 of each of the tines 165. The tip 172 facilitates anchoring when the medical device 150 is inserted into a patient.

Figure 4:
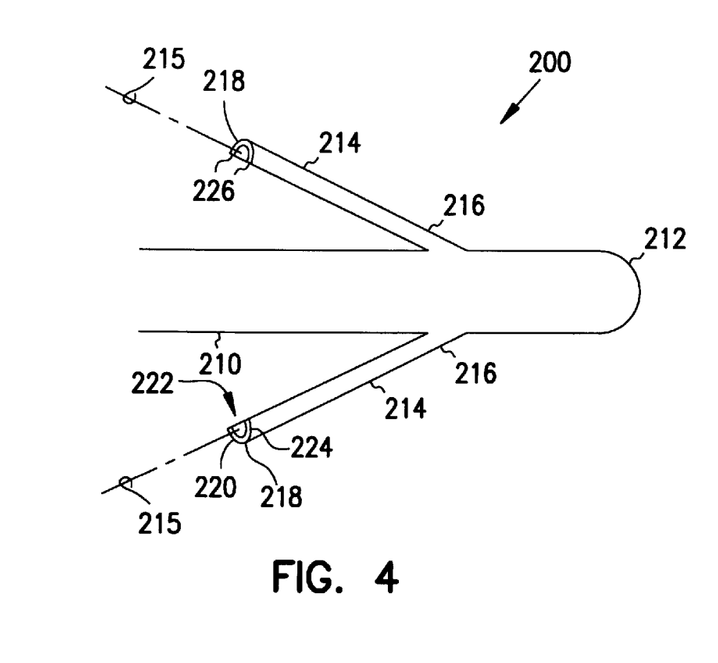
FIG. 4 is an elevational view illustrating a distal tip electrode constructed in accordance with one embodiment of the present invention.
Figure 5:
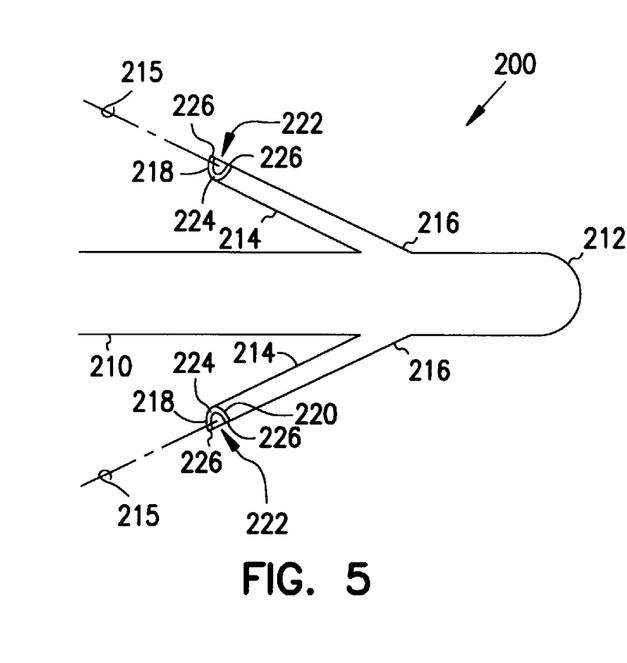
FIG. 5 is an elevational view illustrating a distal tip electrode constructed in accordance with another embodiment of the present invention.

FIGS. 4 and 5 illustrate yet another embodiment of the present invention. A medical device 200 is provided which includes a plurality of tines 214 coupled therewith. In one embodiment, the medical device 200 includes an electrode 202 which includes an electrode assembly 204. The medical device 200 includes a body 210 which extends to a tapered portion 212 to facilitate insertion of the body 210 into a patient. The plurality of tines 214 are coupled with the body 210 and are adapted to be collapsible during implantation of the medical device 200, yet are also adapted for anchoring the medical device 200 within the patient.

The tines 214 are defined in part by a radial axis 215, and extend from a coupling end 216 to a free end 218. The plurality of tines 214 are attached to the body 210 of the medical device 200 at the coupling end 216 of the plurality of tines 214. The free end 218 is disposed away from the body 210 of the medical device 200 such that the plurality of tines 214 are angled away from the body 210 of the medical device 200.

In one embodiment, the plurality of tines 214 each have a semi-circular cross section 220. The semi-circular cross section 220 includes an open portion 222 and a curved portion 224. The open portion 222, in one embodiment, is disposed toward the body 210 of the medical device 200 before the tines 214 are collapsed against the body 210. In another configuration, the profile of the open portion 222 corresponds to the shape as the body 210. The curved portion 224 forms the outer arcuate portion of the semi-circular cross section 220 shown in FIG. 4. The curved portion 224 extends to free edges 226 forming a channel 228 therebetween.

In yet another configuration, as shown in FIG. 5, the plurality of tines 214 have a semi-circular cross section 220. The semi-circular cross section 220 is disposed such that the curved portion 224 is placed adjacent the body 210 of the medical device 200 as the plurality of tines 214 are collapsed upon the body 210. In this configuration, the open portion 222 faces away from the body 210 as the plurality of tines 214 are collapsed against the body 210.

Figure 6:
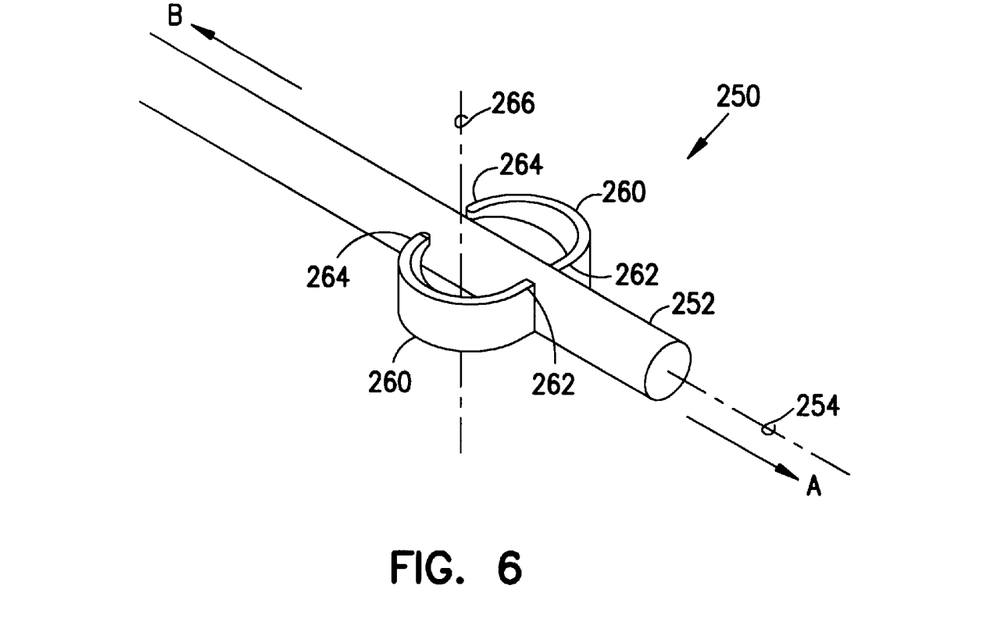
FIG. 6 is an elevational view illustrating a distal tip electrode constructed in accordance with one embodiment of the present invention.

FIG. 6 illustrates yet another embodiment of the present invention. A medical device 250 is provided with a plurality of tines 260. The plurality of tines 260, as well as the tines discussed in the above embodiments, are adapted to be collapsible during insertion of the medical device 250 into a patient, as the medical device 250 is inserted in the direction denoted as "A" on FIG. 6. Alternatively, in another embodiment, the tines 260 are disposed in the opposite direction, for instance when the medical device 250 is inserted in the direction denoted as "B" on FIG. 6.

Figure 7:
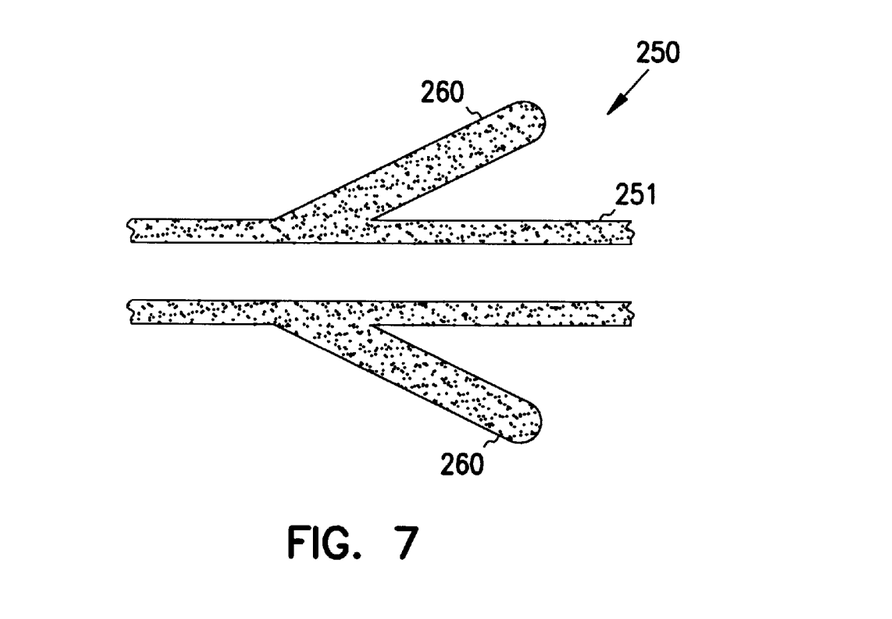
FIG. 7 is a cross-sectional view illustrating an electrode constructed in accordance with one embodiment of the present invention.

The tines 260 also provide a mechanism which is also adapted for anchoring the medical device 250 against inadvertent removal from the patient, and/or provides for compressibility of the tines 260 which assists in deployment of the medical device 250 through the patient. The plurality of tines 260, in one embodiment, are formed from a flexible material, such as silicone, polyurethane, or fluropolymers (e.g. PTFE, ETFE, FEP, PFA). Alternatively, the plurality of tines 260 are formed from other materials, such as a bioresorbable material. In another embodiment, the bioresorbable material, or the above suggested materials, is formed in a foam consistency, as illustrated in FIG. 7. In addition at least a portion of the body 251 of the medical device 250 can also be formed of a foam material such that the body 251 can also be compressed. The foam construction could be an open-cell structure, where the void cells are interconnected with tunnels. Alternatively, the foam construction could be a closed-cell structure. In addition, the foam density can be varied to achieve variations in rigidity. In yet another embodiment, a syntactic foam structure is used which includes a polymer matrix and fillers of hollow spherical particles. The particles, which can also be gas filled, are distributed throughout the matrix. A further embodiment is to form the polymer matrix of the foam as a blend or alloy or two or more polymers.

The bioresorbable material allows for temporary anchoring of the medical device 250 within the patient while tissue grows about the medical device 250 to form a more permanent anchoring structure. These different materials can also be used for the earlier discussed embodiments as well.

Figure 9:
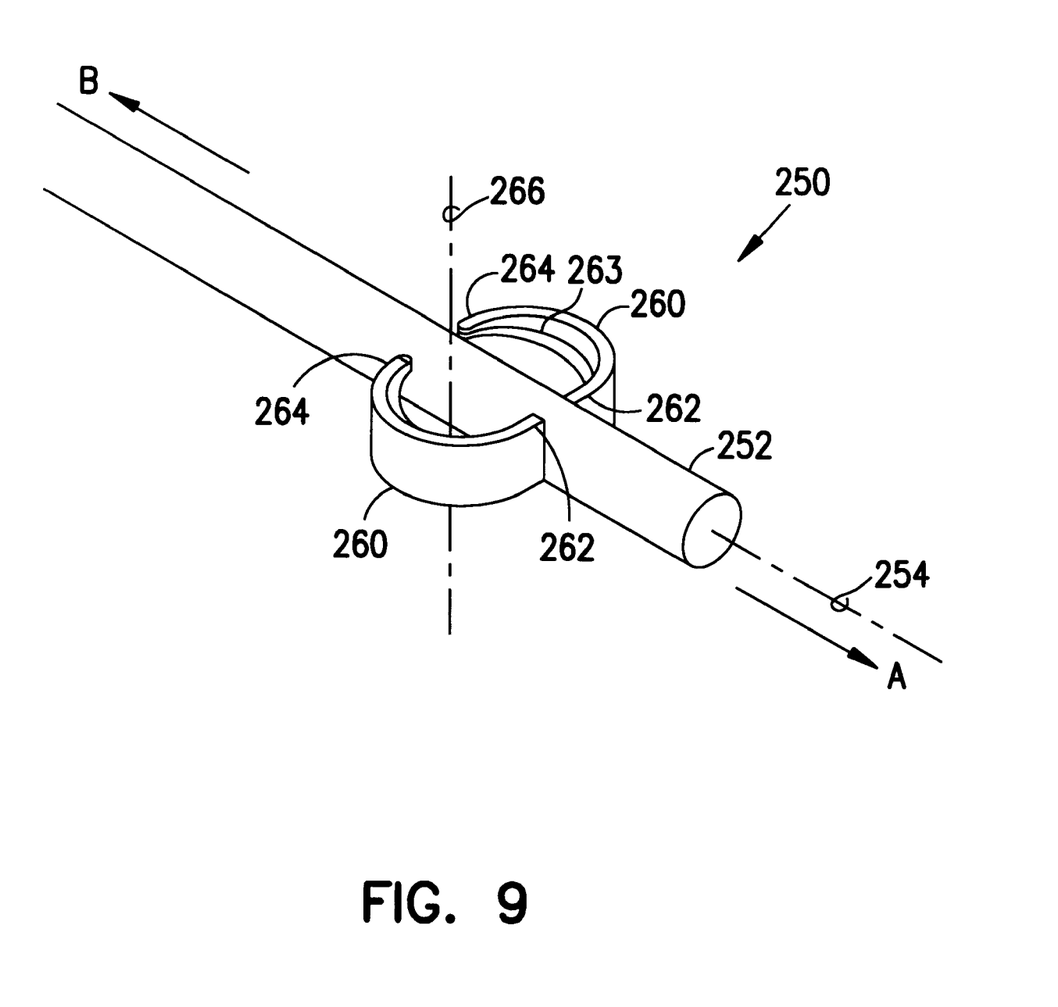
FIG. 9 is an elevational view illustrating a distal tip electrode.

The plurality of tines 260 extend from a coupling end 262 to a free end 264. The plurality of tines 260 are attached to the medical device 250 at the coupling end 262 of the plurality of tines 260. Optionally, the at least one tine 260 has a slit 263 therein, as shown in FIG. 9 The plurality of tines 260 form an arcuate shape which extends from the coupling end 262 to the free end 264 forming a coiled structure having an axis 266. In one configuration, the axis 266 of the each of the plurality of tines 260 is disposed transverse to a radial axis 254 of the medical device 250.

The plurality of tines 260 are attached to the medical device 250 in a number of manners. In one configuration, the plurality of tines 260 are molded with the molding of the medical device 250. Alternatively, the plurality of tines 260 are secured to the medical device 250 in other manners. For instance, in one embodiment, the plurality of tines 260 are bonded to the body of the medical device 250.

Figure 8:
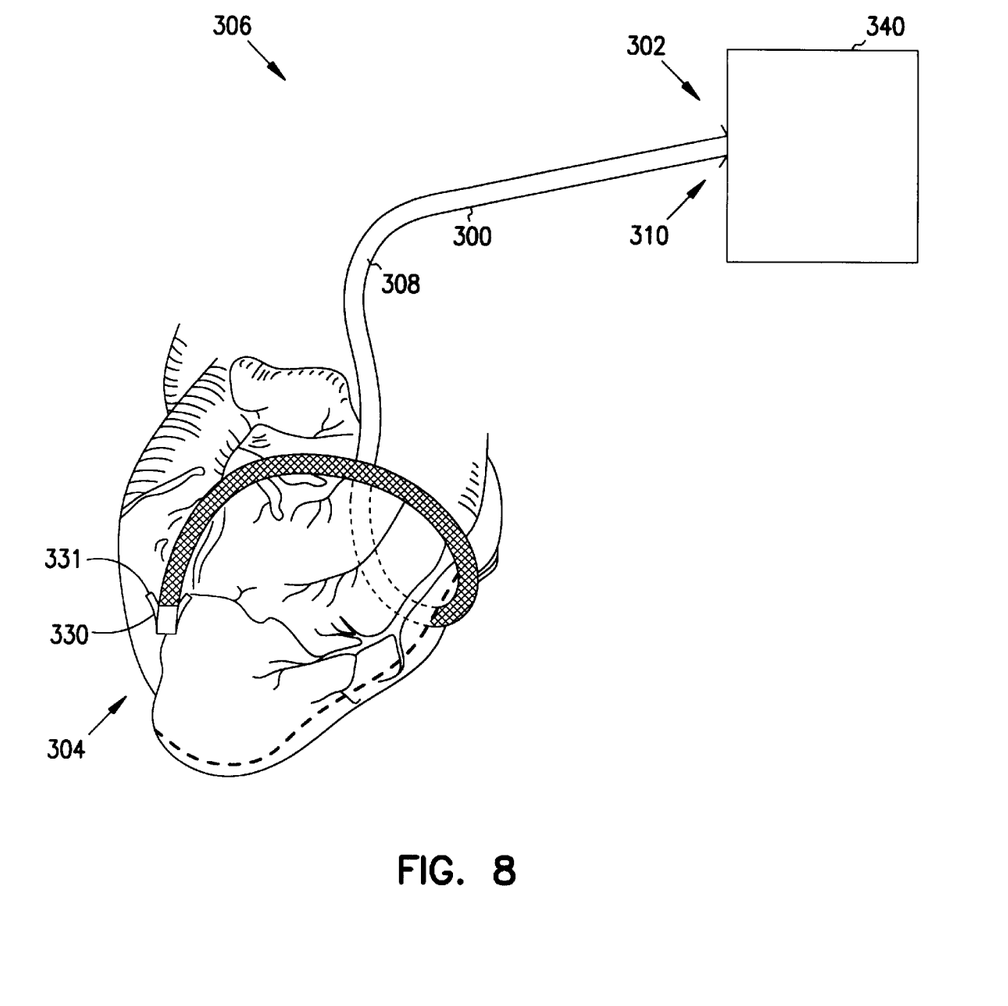
FIG. 8 is a block diagram illustrating a distal tip electrode for use with a monitoring and pacing system constructed in accordance with one embodiment of the present invention.

FIG. 8 illustrates another embodiment a lead 300 for use with a system 306 which is adapted for delivering electrical pulses to stimulate the heart. The lead 300 is not limited to any particular type of lead. The lead 300 extends from a proximal end 302, which is adapted to connect with equipment which supplies electrical pulses, to a distal end 304 which is adapted to be inserted into the heart.

Proximate to the distal end 304 is an electrode tip 330. The electrode tip 330 includes a plurality of tines 331 coupled therewith. As the electrode tip 330 is inserted through the patient, the plurality of tines 331 collapse against a body 308 of the lead 300.

Proximate to the proximal end 302 of the lead 300 is a connector terminal 310. The connector terminal 310 electrically connects the various electrodes and conductors within the lead 300 to a pulse generator and signal sensor 340. The pulse sensor and generator 340 contains electronics to sense various electrical signals of the heart and also produce current pulses for delivery to the heart, depending on the type of lead 300 used. The pulse sensor and generator 340 also contains electronics and software necessary to detect certain types of arrhythmias and to correct for them. The lead terminal connector 310 provides for the electrical connection between the lead 300 and the pulse generator 340.

Advantageously, the hollow tines of the medical device can collapse to a low profile when passing through restricting diameters such as introducers or vasculature, thus creating minimal drag during placement of the medical device. When unrestricted by the restricting diameters, the construction of the tines of the medical device are adapted to offer rigidity that will cause the plurality of tines to stand out away from the medical device body, thereby creating a mechanism for anchoring the medical device. One example of a medical device which is useful with the plurality of tines is a lead placement. When the tines are used in combination with the lead, the lead can be anchored within a heart chamber using the tines as a passive fixation until tissue end-growth occurs. Alternatively, the lead can be introduced intravenously as the tines collapse to a low profile.

Collapsible tines aid in providing a lead which is atraumatic to the vessel walls, and also provides resistance to dislodgement of the lead from the patient. The collapsible feature of the lead also allows for a smaller introducer to use for a patient which provides for a less traumatic implant for the patient. In addition, collapsibility of the lead could also allow a physician to use a larger introducer yet pass two leads through the introducer. The hollow collapsible tines are not limited to any type of medical device, or any type of lead.

The anchoring mechanism of the tines assists in preventing inadvertent dislodgement of the lead from the patient, yet allows for removal of the lead should that be necessary. In addition, lead deployment is improved since compressibility of the medical device is improved and the amount of drag is reduced as the lead is displaced through a vein. The increased compressibility allows a practitioner to use smaller devices which reduces complications and trauma to the patient. This allows for flexibility in insertion of the lead adjacent the heart wall, as is commonly used for lead placement proximate the left chamber of the heart. It should be noted, however, that the lead can be placed in either the left or right chamber of the heart.

It is to be understood that the above description is intended to be illustrative, and not restrictive. Many other embodiments will be apparent to those of skill in the art upon reviewing the above description. For instance, the plurality of tines can be used with a wide variety of medical devices. The scope of the invention should, therefore, be determined with reference to the appended claims, along with the full scope of equivalents to which such claims are entitled.

What is claimed is:

1. A lead adapted for implantation in, on, or about the heart, said lead comprising:

an electrode assembly including at least one electrode and at least one collapsible tine coupled therewith, the electrode assembly coupled with a lead body;

the at least one tine being at least partially hollow, wherein the at least one tine has a semi-circular cross-section;

the semi-circular cross-section having an open portion, the open portion being disposed away from the lead body.

2. A lead adapted for implantation in, on, or about the heart, said lead comprising:

an electrode assembly including at least one electrode and at least one tine coupled therewith, the electrode assembly coupled with a lead body;

the at least one tine being at least partially hollow; and the at least one tine extends from a coupling end to a free end, where the coupling end is attached to the lead body and the free end is cut at an angle, the free end having an elliptical opening.

3. The lead as recited in claim 1, wherein the at least one tine is molded to the lead body of the electrode assembly.

4. The lead as recited in claim 1, wherein the at least one tine is bonded to the lead body of the electrode assembly.

5. The lead as recited in claim 1, wherein the at least one tine is formed from silicone material.

6. The lead as recited in claim 1, wherein the at least one tine is formed from bioresorbable material.

7. The lead as recited in claim 1, wherein the at least one tine is formed from polyurethane.

8. The lead as recited in claim 1, wherein the at least one tine is formed from foam.

9. A lead adapted for implantation in, on, or about the heart, said lead comprising:

an electrode assembly including at least one electrode and at least one tine coupled therewith, the electrode assembly coupled with a lead body;

the at least one tine being at least partially hollow;

the lead body further comprising a recess adapted to receive a portion of the at least one tine therein.

10. The lead as recited in claim 9, further comprising a ring coupling the at least one tine with the lead body within the recess.

11. A lead adapted for implantation in, on, or about the heart, said lead comprising:

an electrode assembly including at least one electrode and at least one tubular tine coupled therewith, the electrode assembly coupled with a lead body; and the at least one tine extends from a coupling end to a free end, and the free end has a larger cross-section than the coupling end.

12. The lead as recited in claim 2, wherein the at least one tine extends from a coupling end to a free end, and the at least one tine is tapered from the free end to the coupling end.

13. The lead as recited in claim 9, wherein the at least one tine is collapsible.

14. A lead adapted for implantation in, on, or about the heart, said lead comprising:

an electrode assembly including at least one electrode and at least one collapsible tine coupled therewith, the electrode assembly coupled with a lead body; and the at least one tine radially extending from a coupling end proximate to the lead body to a free end, the at least one tine having a coiled structure, and the at least one tine adapted to be disposed in a first uncollapsed position and a second collapsed position, where the free end is free from the lead body in the first and second positions.

15. The lead as recited in claim 11, wherein the at least one tine comprises a semi-circular structure.

16. The lead as recited in claim 11, wherein the at least one tine comprises a thin-walled circular structure.

17. The lead as recited in claim 14, wherein the at least one tine is bonded to the electrode assembly.

18. The lead as recited in claim 14, wherein the at least one tine is formed from silicone material.

19. The lead as recited in claim 14, wherein the at least one tine is formed from bioresorbable material.

20. The lead as recited in claim 14, wherein the at least one tine is formed from polyurethane.

21. The lead as recited in claim 14, wherein the at least one tine has a slit therein.

22. A system for monitoring or stimulating cardiac activity comprising:

a pulse sensor and signal generator adapted for receiving and producing pulses to apply to the heart;

a lead extending from a proximal end to a distal end, the proximal end of the lead being operatively coupled with said sensor and generator;

an electrode assembly disposed proximate to the distal end of the lead;

the electrode assembly including at least one foam tine coupled therewith; and the at least one tine being at least partially hollow.

23. The system as recited in claim 22, wherein the at least one tine has a semi-circular cross-section.

24. A lead adapted for implantation in, on, or about the heart, said lead comprising:

an electrode assembly including at least one electrode and at least one tine coupled therewith, the electrode assembly coupled with a lead body;

the at least one tine formed of a foam material.

25. The lead as recited in claim 24, wherein the at least one tine is at least partially hollow.

26. The lead as recited in claim 24, wherein the foam comprises an open-cell structure.

27. The lead as recited in claim 24, wherein the foam comprises a closed-cell structure.

28. The lead as recited in claim 24, wherein the foam comprises a syntactic foam structure.

29. A lead adapted for implantation in, on, or about the heart, said lead comprising:

an electrode assembly including at least one electrode and at least one tine coupled therewith, the electrode assembly coupled with a lead body, wherein the lead body further comprises a recess adapted to receive a portion of the at least one tine therein;

the at least one tine being at least partially hollow and comprises a thin-walled circular structure, the at least one tine extends from a coupling end to a free end, where the coupling end is attached to the lead body and the free end is cut at an angle;

wherein the at least one tine extends from a coupling end to a free end, and the free end has a larger cross-section than the coupling end; and a ring coupling the at least one tine with the lead body within the recess.

30. The lead as recited in claim 15, wherein the at least one tine is at least partially hollow.

31. The lead as recited in claim 14, wherein the at least one tine radially extends about a radial axis disposed transverse to an axis of the lead body.

32. The lead as recited in claim 14, wherein the at least one tine is molded to the electrode assembly.

* * * * *